United States Patent [19]
Hill et al.

[11] Patent Number: 6,060,069
[45] Date of Patent: May 9, 2000

[54] PULMONARY DELIVERY OF PHARMACEUTICALS

[75] Inventors: Malcolm Hill, Solana Beach, Calif.; Peter R. Byron, Richmond, Va.

[73] Assignee: Dura Pharmaceuticals, Inc., San Diego, Calif.

[21] Appl. No.: 09/071,578

[22] Filed: May 1, 1998

Related U.S. Application Data

[63] Continuation-in-part of application No. 08/756,654, Nov. 26, 1996, abandoned, which is a continuation of application No. 08/137,282, Oct. 14, 1993, Pat. No. 5,577,497, which is a continuation-in-part of application No. 07/963,409, Oct. 19, 1992, abandoned, which is a continuation of application No. 07/702,297, May 20, 1991, Pat. No. 5,327,883.

[51] Int. Cl.$^7$ ............................................... A61K 9/12
[52] U.S. Cl. ........................ 424/400; 424/46; 514/826
[58] Field of Search ....................... 424/45, 46; 514/826

[56] References Cited

U.S. PATENT DOCUMENTS 5,225,183  7/1993  Purewal et al. ............................ 424/45
5,674,471 10/1997  Akehurst et al. .......................... 424/45

FOREIGN PATENT DOCUMENTS

97/40819  11/1997  WIPO .

OTHER PUBLICATIONS

Morén, F. (1993) Aerosols in Medicine: Principle, Diagnosis and Theraby, Chapter 13, pages 321–350. Elsevier Science Publishers, Netherlands.

*Primary Examiner*—Raj Bawa
*Attorney, Agent, or Firm*—Lyon & Lyon LLP

[57] ABSTRACT

In a method for treating lung diseases, a drug formulation is prepared by combining micronized crystalline beclomethasone dipropionate and lactose. The drug formulation is placed into a dry powder inhaler which provides inhalable drug particles having a mass median diameter of about 0.5–5.8 microns. The inhaler is preferably largely flow rate independent. Drug and lactose particles are separated in the inhaler during inhalation, most desirably via a spinning element. Due to deep deposition, the drug particles persist in the lungs for a surprisingly long duration, increasing the therapeutic effect of each dose. The patient inhales the drug particles with an inspiratory flow rate of about 10–60 liters/minute, to produce a deep lung deposition of inhaled particles.

18 Claims, 6 Drawing Sheets

PULMONARY DELIVERY OF PHARMACEUTICALS

This application is a continuation-in-part of Ser. No. 08/756,654, incorporated herein by reference, filed Nov. 26, 1996, and now abandoned, which in turn is a continuation of Ser. No. 08/137,282, filed Oct. 14, 1993, now U.S. Pat. No. 5,577,497, which is a continuation-in-part of Ser. No. 07/963,409, filed Oct. 19, 1992 and now abandoned, which in turn is a continuation of Ser. No. 07/702,297, filed May 20, 1991, now U.S. Pat. No. 5,327,883.

BACKGROUND OF THE INVENTION

Drug delivery by inhalation is the preferred route of administration for drugs whose site acting in the lungs. Currently, the metered dose inhaler (MDI) is the most prescribed method of delivering drugs to the lungs. The MDI is the present method of choice because of its high degree of patient acceptance, relative simplicity of use, portability, and multiple-dose capacity. However, the majority of MDIs use chlorofluorcarbons (CFCs) as the system propellant. Due to increasing concerns over the potential adverse effects of CFCs on the atmosphere and the environment, and the international restrictions phasing-out their production over the next several years, alternative systems of aerosolized drug deliver are being developed. MDIs also require a degree of coordination to use. The patient must synchronize inhaling with release of a drug dose. For many patients, this synchronization is difficult to achieve.

Dry powder inhalers (DPI's) deliver a drug powder in an aerosol stream, to be inhaled directly into the lungs without the use of propellants, chlorinated or halogenated. The Spiros® DPI developed by Dura Pharmaceuticals, Inc., San Diego, Calif., is a multiple-dose, breath-actuated battery-powered, pocket-size delivery system that requires minimal patient coordination. Powder delivery takes place only upon patient inspiratory breathing and is largely independent of inspiratory flow rate, as described in U.S. Pat. Nos. 5,327,883 and 5,577,497, incorporated herein by reference. The Spiros DPI has a molded body with a removable mouthpiece and a disposable multiple-dose drug cassette loaded with 30 individual doses of drug product. The patient's inspiratory flow actives a battery-powered twin-blade impeller, creating a powder aerosol cloud which is inhaled during inspiration. The motor-driven impeller allows the Spiros DPI to operate relatively independent of inspiratory flow rate over the wide range of patient-specific flow rates typically observed in asthmatic children and adults.

Inspiratory flow rate is the air velocity a patient generates when inhaling. In healthy adults during tidal breathing, inspiratory flow rate is about 15 L/min, and with effort, inspiratory flow rates of 100 L/min or more are easily achievable. Inspiratory flow rate in adult patients with moderate to severe obstructive airways disease (mean % $FEV_1$ of 38.6% predicted) has been demonstrated to average 25.4 L/min (range 13.3 to 50.4 L/min). In normal children and adolescents (3.5 to 15 yrs) breathing through a Turbuhaler® DPI, only about ⅓ were able to generate an inspiratory flow rate of >60 L/min necessary to create an optimal aerosol from this device.

Perhaps more concerning is the effect of acute wheeze on inspiratory flow rate in asthmatics. It has been demonstrated that 70% of asthmatic children with acute wheeze were only able to generate inspiratory flow rates of <50 L/min breathing through the Rotahaler® DPI, which was significantly lower than their inspiratory flow rate measured when these children were stable. Since asthma is an obstructive airways disease, it may have a dramatic effect on the ability of adults and children with asthma to create an inspiratory flow rate adequate to operate most DPI's currently available. For example, the Turbuhaler® DPI (Astra/Draco, Sweden) and the Ventodisk® DPI (Glaxo, UK) have respirable percentages determined by twin impinger of <8.9% of 15 L/min, which increase to >35% at 60 L/min.

Consequently, while DPI's have several advantages over MDI's, DPI's have not yet found as much widespread acceptance, in part because of their flow rate characteristics, especially as they relate to patients having obstructive or inflammatory lung conditions, such as asthma. The Spiros inhaler, which is now in clinical evaluation, overcomes these well known difficulties associated with DPI's.

SUMMARY OF THE INVENTION

In a method for treating lung diseases, a drug formulation is prepared by combining micronized crystalline beclomethasone diprionate (BDP) and lactose. The drug formulation is placed into a dry powder inhaler which provides inhalable drug particles having a mass median diameter of about 0.5–5.8 microns. The inhaler is preferably largely flow rate independent. Drug and lactose particles are separated in the inhaler during inhalation, most desirably via a spinning element. The patient inhales the drug particles with an inspiratory flow rate of about 10–60 liters/minute, to produce a deep lung deposition of inhaled particles. Due to deep deposition, the drug particles persist in the lungs for a surprisingly long duration, increasing the therapeutic effect of each dose.

The method delivers solid crystalline microparticulate BDP by oral inhalation into the lungs, and results in prolonged plasma half-ines of BDP, relative to those seen following delivery by a metered dose inhaler. The prolonged plasma half lives are indicative of or due to: 1] Rate limiting drug absorption from the lung into plasma. Absorption into plasma is slower than elimination from the plasma, and terminal elimination half-lives in plasma is controlled by the kinetics of drug absorption; 2] Reduced clearance rates from the airways of the lungs, due to drug deposition in the lung regions which are poorly accessed by the mucocilliary clearance mechanisms which are prevalent in conducting airways of the lung. The drug deposition is conferred by use of a BDP formulation and aerosol generation, and human administration technology which is suitable for delivery of drug much deeper into the lung than is normally achieved by delivery of crystalline BDP from a metered dose inhaler.

BRIEF DESCRIPTION OF THE DRAWINGS

In the drawings, wherein similar reference numbers denote similar elements;

FIG. 1 is a perspective view of a Spiros inhaler;

FIG. 2 is a perspective view of the inhaler shown in FIG. 1, with the mouthpiece removed;

FIG. 3 is a section view of the inhaler shown in FIG. 1;

FIG. 4 is an unweighted graph of blood concentration of BDP over time;

FIG. 5*a* is a 1/y weighted graph thereof;

FIG. 5*b* is a kinetic model;

FIG. 6 is a graph of a mathematical model of BDP in the lungs after delivering a dose via an MDI; and FIG. 7 is a graph thereof after delivering a dose via the Spiros DPI.

DETAILED DESCRIPTION OF THE PREFERRED EMBODIMENT

Figure 1:
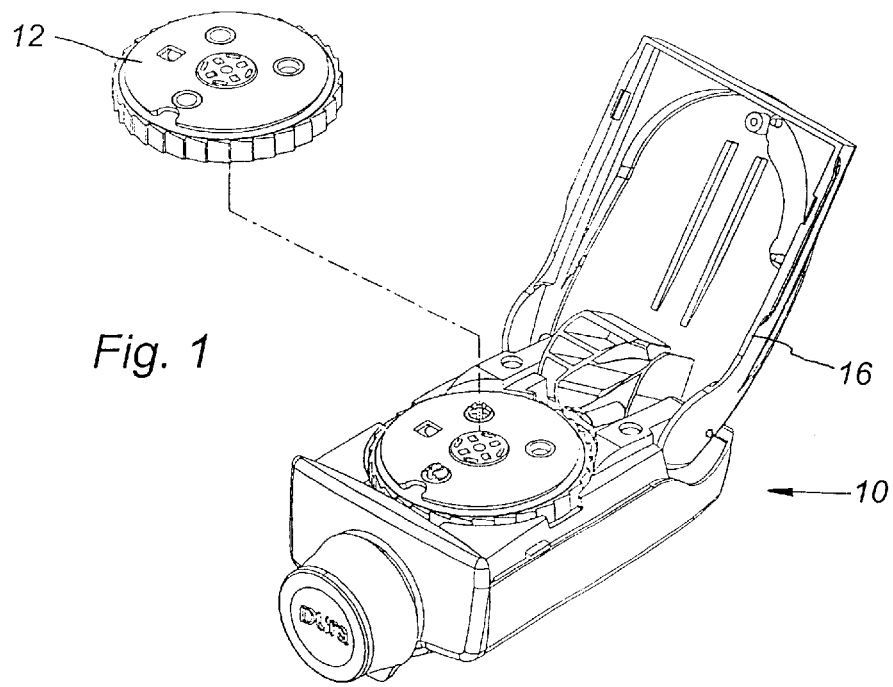
Figure 2:
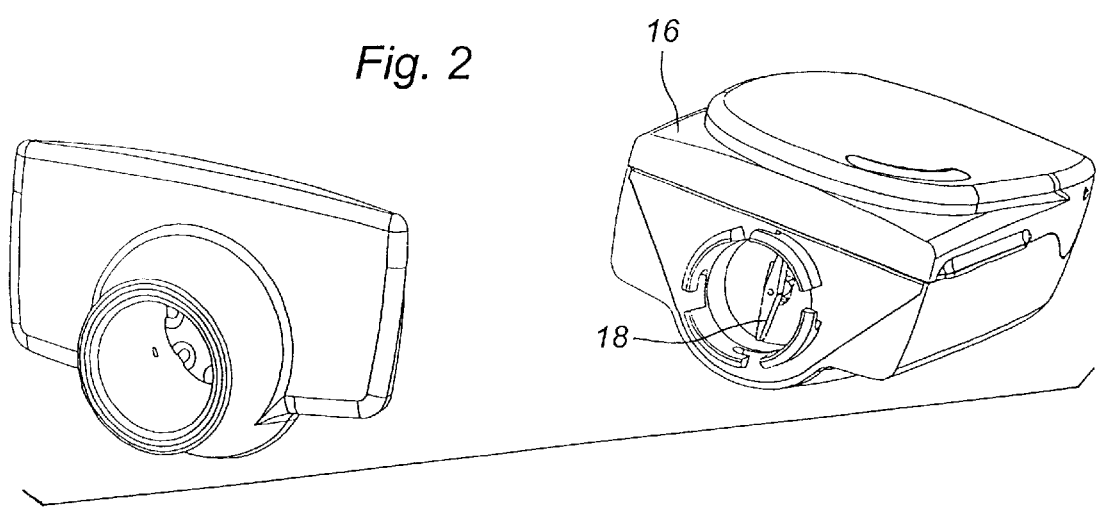

As shown in FIG. 1, the Spiros DPI 10 is a small (4 cm×10 cm×6 cm), reusable delivery system. The Spiros DPI is breath-actuated, which minimizes the need for patient coordination. Unit doses of an inhalable pharmaceutical powder are contained in a circular multiple dose cassette 12 which contains 30 dosage wells and fits snugly into the Spiros DPI. A dose is indexed into the aerosolization chamber 14 by first opening the lid 16 approximately 135° and then shutting it. The breath-actuated, twin-bladed impeller 18 spins at very high r.p.m. inside the chamber 14, driven by an electric motor, to generate an aerosol cloud of air and pharmaceutical powder.

Figure 3:
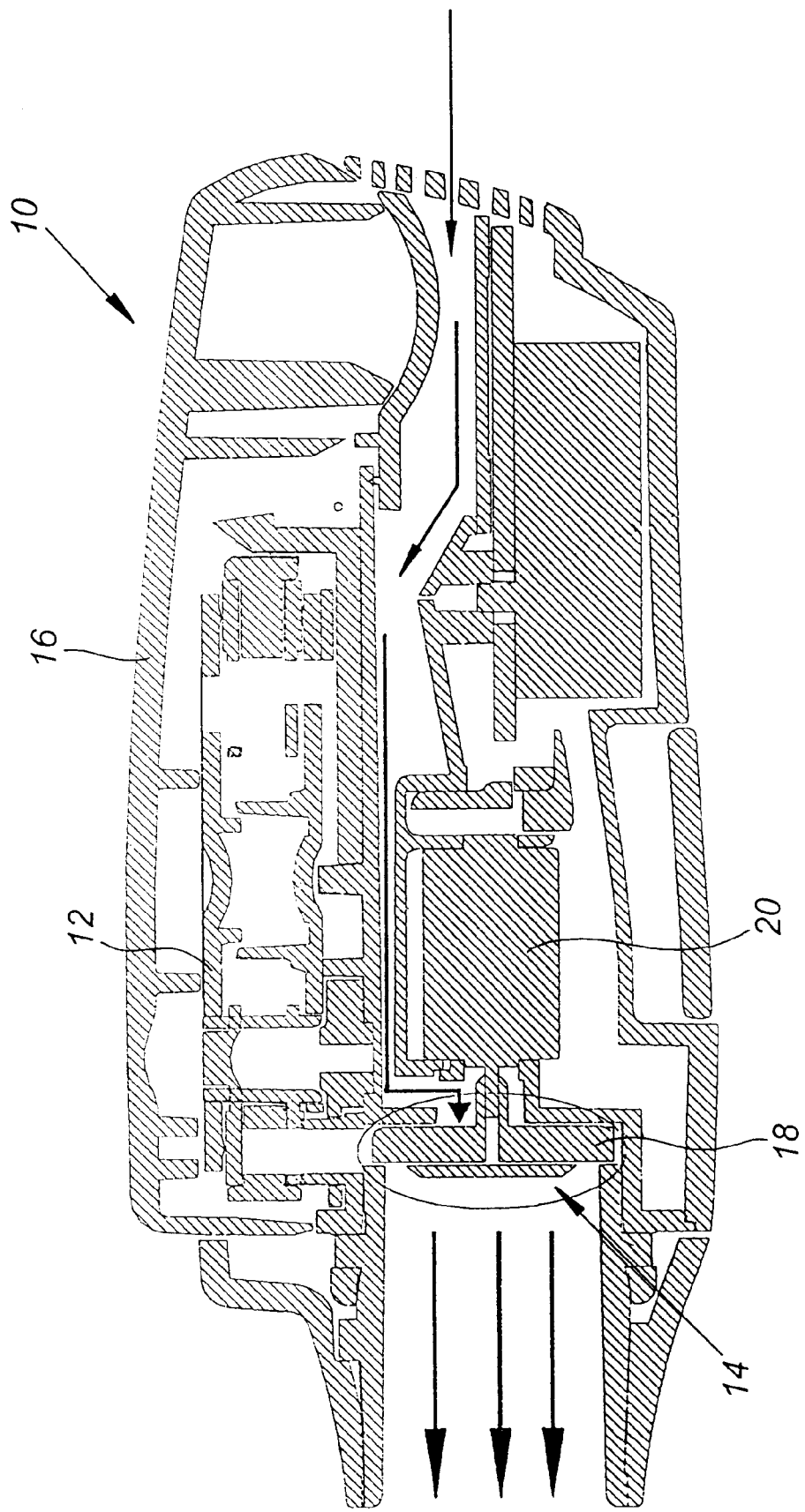

Negative intra-airway pressure generates an airstream which travels around the impeller hub, carrying the aerosol plume through radially arranged holes into the mouthpiece area. As shown in FIG. 3, ducts in the mouthpiece area are arranged bilaterally to intensify and focus the airstream during inspiration, carrying the aerosol plume into the airways of the patient

The Pharmaceutical Formulation

The Spiros DPI can delivery different drugs. A preferred drug for treating asthma is beclomethasone dipropionate.

A beclomethasone dipropionate (BDP) formulation is prepared by first micronizing through conventional means (e.g., a jet mill) to produce a range of particle sizes that are likely to undergo sedimentation in the human airway. Generally, fine particles in the range of 0.5 to 5.8 microns in diameter are thought to undergo sedimentation between the oropharynx and small bronchioles. Particles within this general size category are thought to be in the "respirable range." Such micronized materials have excessive surface free energy, and as a result have a tendency to adhere strongly to many surfaces, most especially to themselves.

In addition, the dosage of BDP to be delivered is far smaller than can be accurately metered. To overcome these two problems, coarse agglomerates are formed with inert substances such as lactose. Lactose particles in the size range of 20 to 100 microns are mixed with the smaller diameter micronized drug particles to create a homogenous blend. Each lactose particle binds to a number of smaller drug particles in the blend. The blend flows more easily during the packaging and dose metering process.

In the specific formulation used, BPP was micronized to a particle size ranging between 1.1 and 2.6 micron and then blended with the lactose. The formulation was then filled into cassettes, each containing 30 individual doses. The average fill weight for each individual dose was 8 mg±10%, resulting in an average cassette fill weight of 240 mg±10%. The cassettes were then packaged in sealed foil pouches.

BDP is a highly topical active glucocorticoid, yet also has active metabolites, specifically beclomethasone monopropionate (BMP), and to a lesser degree, beclomethasone (B). These metabolites are formed form that port of the dose that is swallowed during the inhalation, as well as in lung tissue, and other tissues in the body. It is important to note that the BDP which is measurable in plasma is due to absorption from lung into the bloodstream, and not any other sources.

Respirable Dose

Key measures used to assess inhalation delivery systems are the respirable dose and its reproducibility in achieving lung deposition under a range of clinical conditions. Several delivery performance factors influence these measures. In designing and evaluating different aerosol delivery technologies, both factors are important. To create an aerosol from a conventional dry powder inhaler, inspiratory flow is one of the most important sources of energy that is used to deagglomerate the powder, i.e., to separate the active drug particles from the lactose. However, the Spiros DPI utilizes a high revolutions per minute (rpm) impeller to deagglomerate the powder and patient inspiratory flow to deliver the powder to the lungs. Deagglomeration of the powder takes place in the aerosolization chamber of the Spiros DPI, via airflow and the mixing/shearing action of the impeller.

The Spiros DPI is an aerosol generation system that is largely independent of the inspiratory flow rate. Because the delivery of the drug is independent of patient inspiratory flow rate and coordination, several important benefits are realized. First, the Spiros DPI can be used by patients with low inspiratory flow rates (such as children, severely compromised patients, or patients experiencing respiratory distress). Currently marketed DPIs deliver different doses depending on inspiratory flow rate. The Spiros DPI, which is largely inspiratory flow rate independent, overcomes these limitations. Second, the currently popular metered dose inhalers (MDI) require significant coordination to use correctly. When the delivery system is manually actuated and drug is delivered in a rapid burst, the time of actuation during the respiratory cycle is crucial. If actuation does not occur at the time of inspiration, the majority of the dose will be deposited in the throat where it provides little or no therapeutic benefit and may cause side effects. The Spiros DPI eliminates the need for patient coordination and timing since the delivery system is breach-actuated.

For inhaled steroids, efficacy is generally believed to be related to the quantity of drug delivered to the intrapulmonary airways. Delivery of drugs to these airways is facilitated by providing an aerosol containing a sufficient quantity of fine particles during the inspiratory phase of the respiratory cycle. This quantity of drug delivered is the respirable dose. The respirable dose is strictly defined as the delivered dose times the fine particle fraction (or respirable fraction). The respirable fraction is that portion of the aerosol of drug exiting the inhaler with a particle size <5.8 :m in diameter. This parameter is typically measured using an Andersen cascade impactor (ACI) at a flow rate of 28.3 L/min.

Beclomethasone dipropionate (BDP) has been commercially available worldwide for more than 20 years, and is one of the most commonly prescribed drugs for the treatment of asthma. It is available in both CFC-based metered dose inhalers (MDIs) and in dry power inhalers (DPIs). Since the delivery and the resulting particle size distributions of BDP from the current commercially available DPIs are highly dependent on flow rate, and thus, quite variable, the performance characteristics of the available MDI systems have been targeted. The performance of these MDI systems is not sensitive to inspiratory flow rate, and therefore, provide a better benchmark.

Loading the Inhaler

The following sequence is used to place a cassette onto the inhaler:
1. The cassette was removed from its sealed foil storage pouch.
2. The lid of the DPI is lifted up to approximately 90 degrees.
3. With the label (and top) up, the cassette is aligned with the two uncovered holes in the cassette over the two alignment posts on the DPI.

4. The cassette is gently pushed down onto the posts until a snap is heard, indicating that the cassette is fully attached.

5. The lid is closed.

Delivering a Dose

The following steps were used to deliver a dose of inhaled drug:

1. The Spiros DPI does not need to be primed.
2. The blue plastic cap is removed from the mouthpiece.
3. The inhaler is held level.
4. The lid of the DPI is opened as far back as possible (The lid will click when it has reached the correct angle).
5. The lid is then closed completely.
6. Before bringing the inhaler up to the mouth, the patient breathes out, making sure not to breathe into the inhaler.
7. The inhaler is brought up to the mouth in a level position.
8. The lips are sealed fully around the mouthpiece, making sure there is no gap between the mouthpiece and the lips.
9. The patient breathes in through the mouth for about 4 seconds, preferably at a flow rate of about 20 LPM. The motor will turn on and the patient may taste/feel the drug as it is inhaled.
10. The patient holds their breath for as long as possible, up to 10 seconds.
11. The Spiros DPI is held in a level position during loading and dosing.
12. To prevent scattering of medication powder, loading a dose without inhaling the medication is avoided.

Two studies were made comparing delivery of BDP via the Spiros inhaler to delivery of an MDI inhaler. The MDI inhaler reference product used was the Vanceril® 42 microgram/actuation emitted dose; Schering-Plough, Kenilworth, N.J. These studies were open label, multiple dose, parallel-group, single-center, investigations conducted with volunteer subjects having mild asthma and not receiving glucocorticoids. The studies measured the pharmacokinetic profile of BDP and its metabolites following inhalation from the Spiros inhaler and the Vanceril MDI. Each study yielded the same results.

In the first of these studies, 23 patients received BDP in an open-label, multiple-dose, parallel-group, single-center, investigation. Patient received a high-dose or low-dose regimen of Spiros BDP or Vanceril for up to 14 days treatment, after which multiple blood samples were obtained, plasma separated and assayed for BDP, BMP, and B concentrations. Plasma BDP concentrations for these treatment regimens are shown in Table 1.

BDP Blood Levels

The data set in Table 1 is the average BDP blood level data from [single] inhalation of 1600 μg doses ex MDI and a Spiros Inhaler [as reported from the first DURA trial protocol DDPIBDP-I-01-0995(b)]. The patients inhaled the known dose and blood samples were taken at the indicated intervals. The BDP in the blood was then measured (at Phoenix International Life Sciences, Montreal, Canada) in picograms/milliliter:

TABLE 1

| Time [min] | BDP [pg/ml]-DPI1600 | BDP [pg/ml]-MDI1600 |
|---|---|---|
| 0 | 0 | 0 |
| 2 | 813.55 | 734.72 |
| 4 | 950.73 | 569.22 |
| 8 | 957.15 | 429.03 |
| 12 | 1123.67 | 293.82 |
| 16 | 922.57 | 188.52 |
| 20 | 973.5 | 95.02 |
| 25 | 666.78 | 81.75 |
| 30 | 815.2 | 68.45 |
| 45 | 447.63 | 23.78 |
| 60 | 371.28 | 0 |
| 90 | 158.33 | 0 |
| 120 | 134.35 | 0 |
| 150 | 73.68 | 0 |
| 180 | 61.06 | 0 |
| 210 | 45.2 | 0 |
| 240 | 31.27 | 0 |

Figure 4:
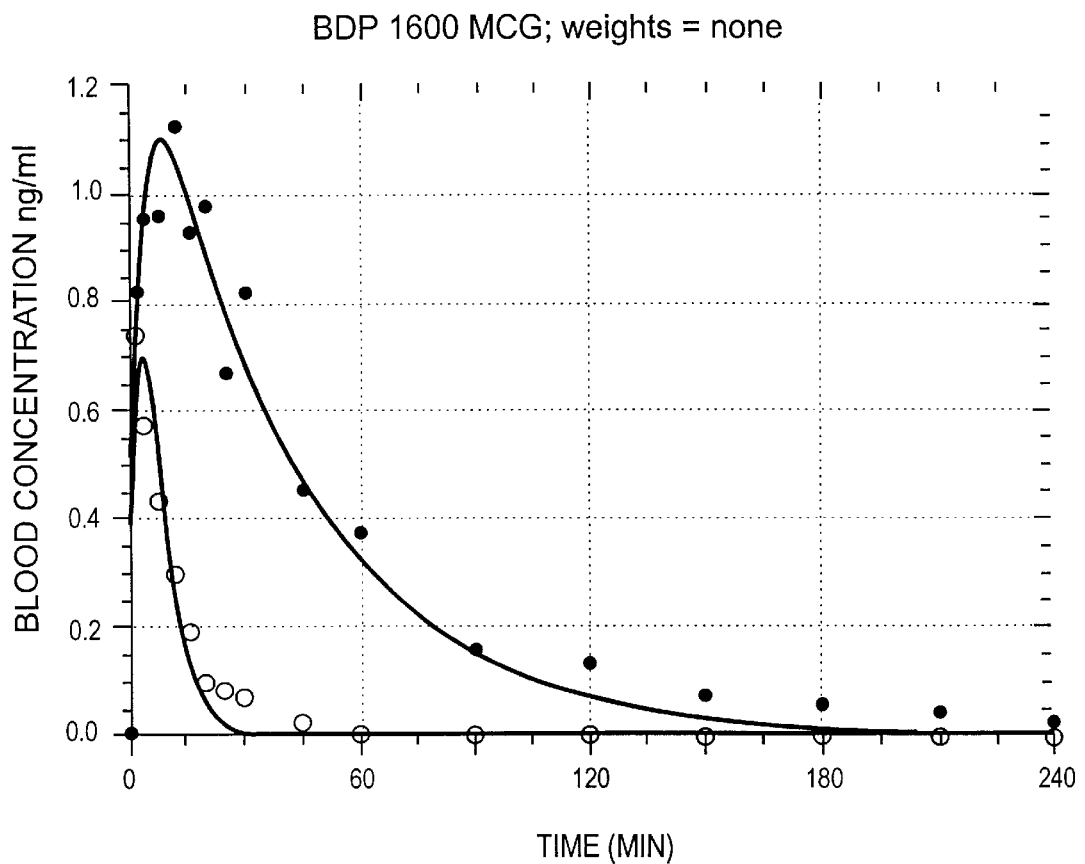
Figure 5A:
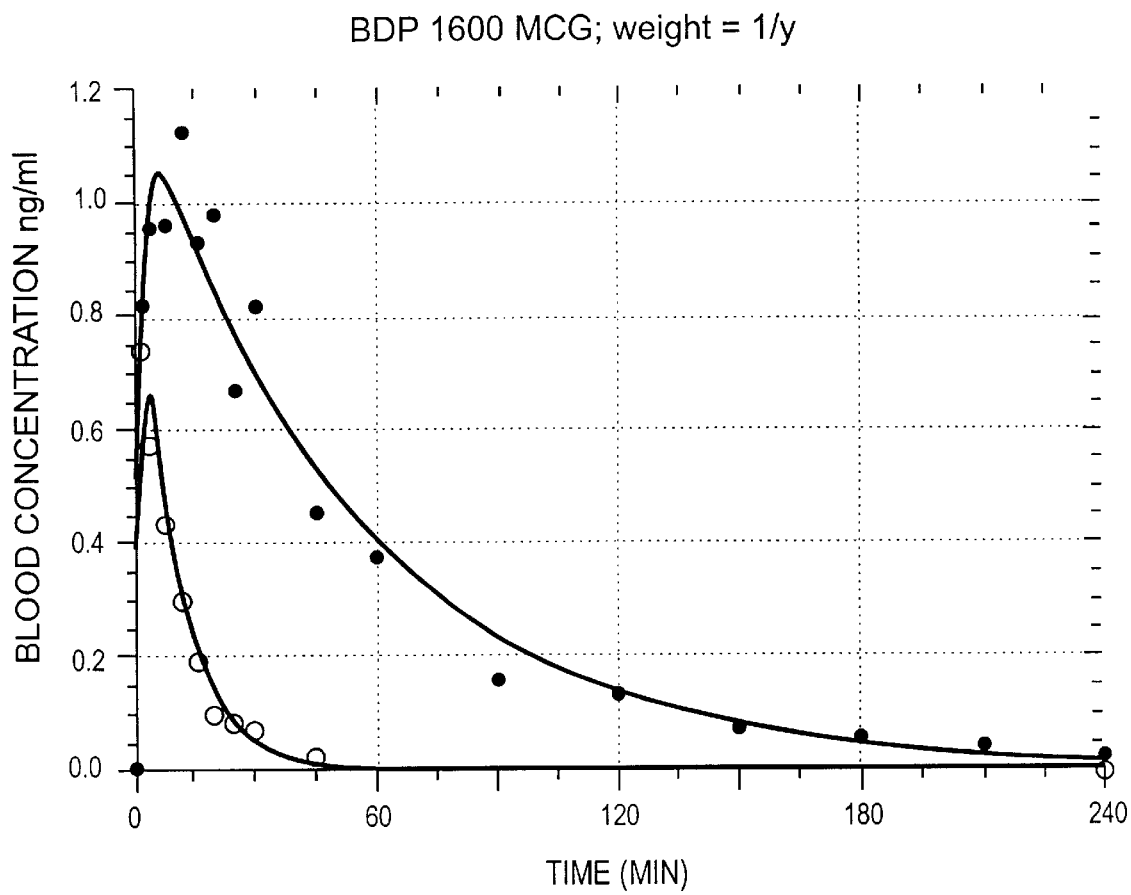
Figure 5B:
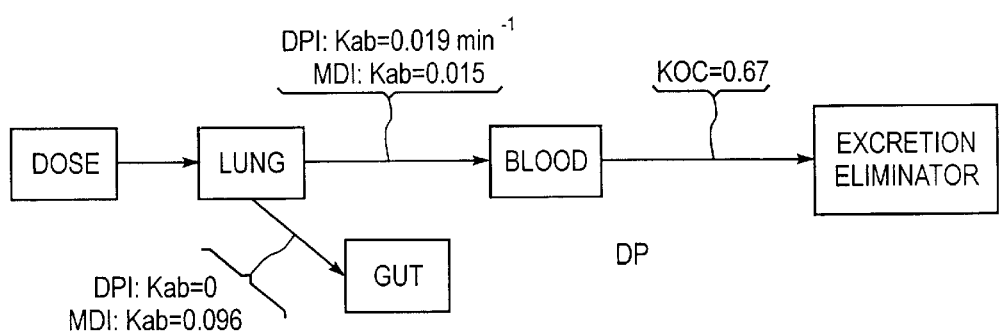

The data in Table 1 are plotted in FIG. 4, the solid points being the DPI 1600 data and the open or circle points being the MDI 1600 data. FIG. 5 shows a similar plot weighted by the reciprocal of concentration.

Figure 6:
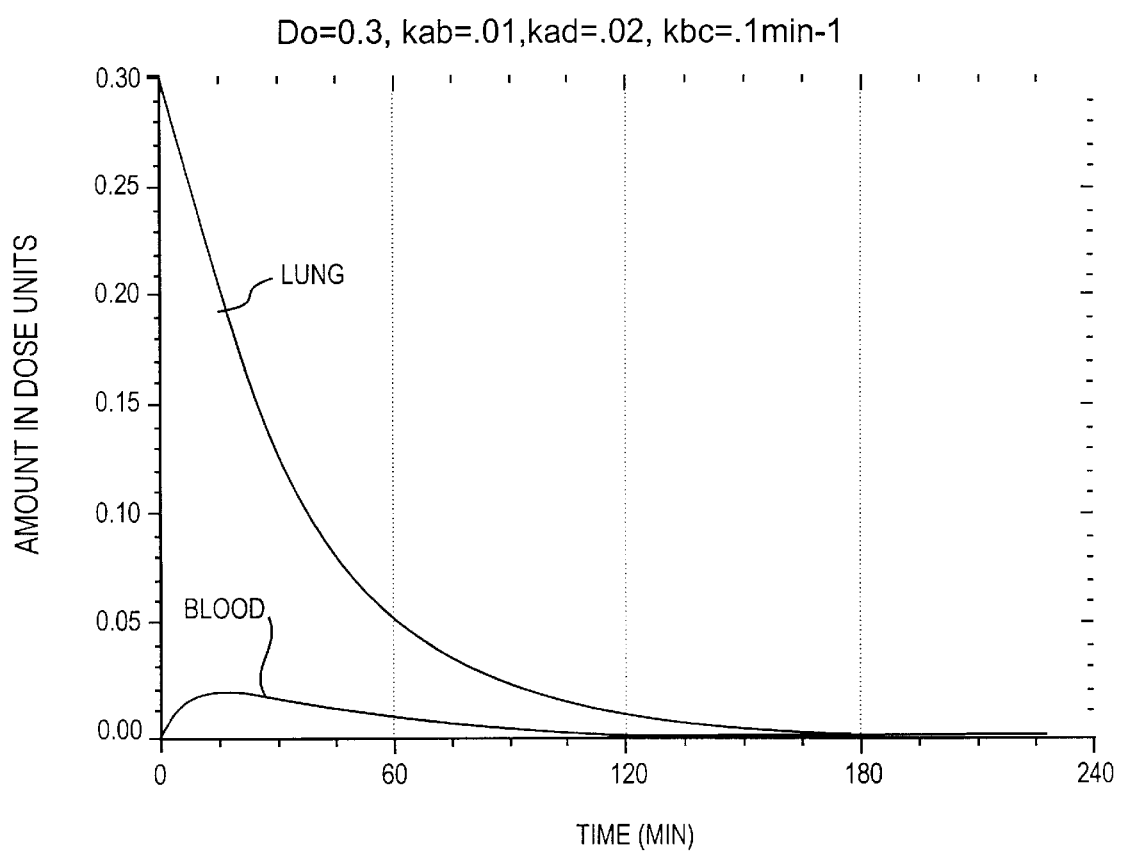
Figure 7:
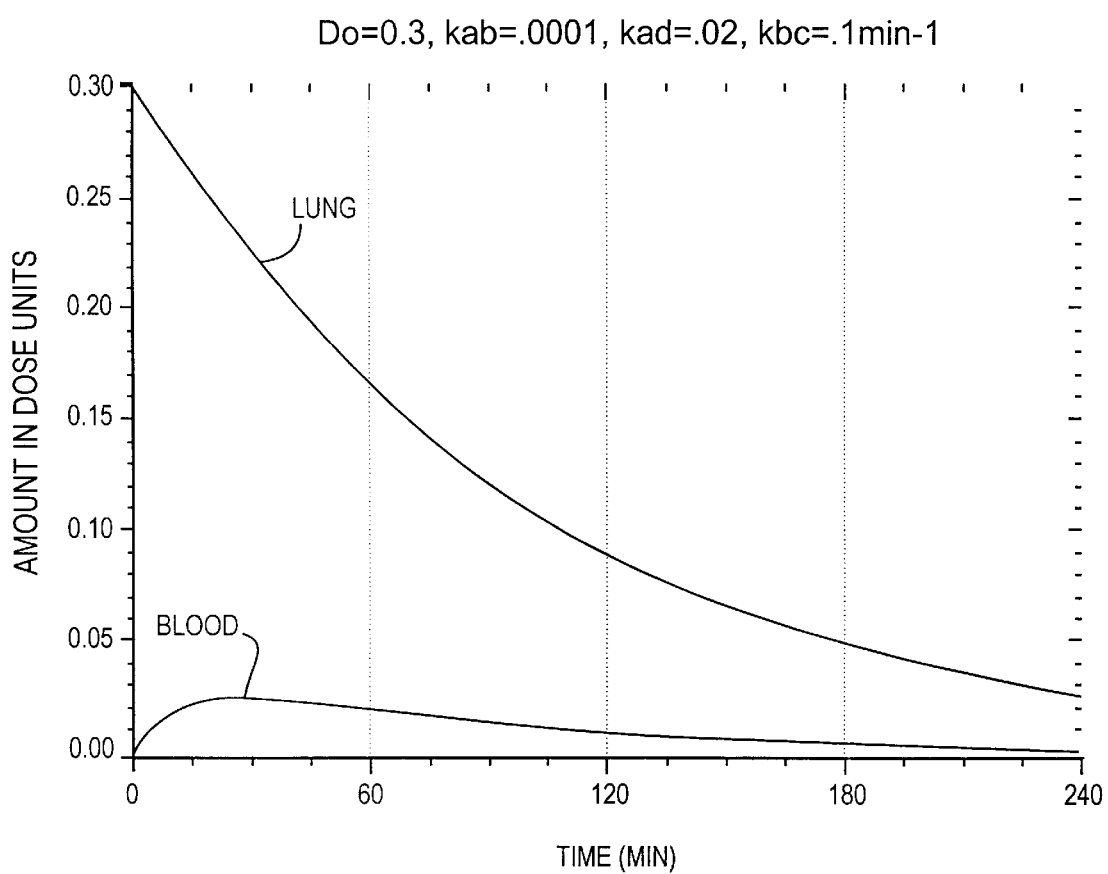

FIGS. 6 and 7 are models of levels remaining over time of BDP in the lung based on the collected data.

Do is the dose normalized into arbitrary dose units.

kab is a rate constant characterizing how fast BDP moves from lung to blood;

kad is a rate constant characterizing how fast BDP moves from lung to gut or local metabolism;

kbc is a rate constant characterizing how fast BDP moves from blood to a metabolized product and elimination.

FIG. 4 shows data points resulting from the study on delivery of BDP from the Spiros and Vanceril inhalers. A series of pharmacokinetic analyses failed to fit the data. The SCIENTIST software (from Micromath, Salt Lake City, Utah) program was then used to fit this data using non-linear regression analysis (based on the kinetic models shown in FIGS. 5b and 6b) and to calculate the best values to use for the rate constants kab, kbc and kad. Table 2 shows the pharmacokinetic parameters for BDP:

TABLE 2

| PARAMETER | MDI | SPIROS |
|---|---|---|
| D/V (dose) | 41584 | 41584 |
| kab | 0.015 | 0.019 |
| kbc | 0.67 | 0.67 |
| kad | 0.096 | 0.00 |

From these data, it can be seen that the major difference in parameters is observed with kad. This suggests that there is little or no mucocilliary clearance of local metabolism that removes BDP from its site of action with the airway with Spiros, relative to MDI (since the kad for MDI is much greater than the kad for Spiros. Additionally, that in the case of Spiros, absorption is slower than elimination, therefor the elimination of BDP from the bloodstream is absorption rate determined. This mechanism, then, describes the slower disappearance of BDP from the bloodstream following dosing with Spiros, and also demonstrates that BDP has a longer residence time at the site of drug action within the airway. Using this mode, the amount of drug remaining in the lung versus time can be calculated, as shown in FIGS. 6 and 7.

The results show the kinetic models are valid, and that the duration of BDP in the lungs was unexpectedly prolonged.

Specifically, the kinetic models show that kad for delivery by the Spiros inhaler is smaller than for the MDI. The decrease in kad correlates to an increase in the half-life of the BDP concentration level in the blood or plasma.

The rate constant kad may change depending on the model used. An important aspect of the invention is that, whatever model is selected, the kad for the BDP delivered via the Spiros inhaler is less than the kad for the reference inhaler or MDI. The figures show kad for the Spiros DPI to be less than half of the kad for the MDI.

With kad=0 in FIG. 7, the prolonged presence of BDP in the lungs can be explained due to low mucocilliary clearance or relative lack of local metabolism. This explanation is consistent with the known laboratory capability of the Sprios® inhaler to provide deep drug delivery to small lung openings, having little or no mucocilliary clearance.

The persistence of BDP in the blood and in the lungs when delivered by the Spiros DPI is surprising.

In view of this surprising achievement, doses may be reduced and/or dosing intervals increased. The therapeutic benefit of the BDP should be enhanced due to its persistence in the lung. The drug advantageously has low solubility so that it dissolves slowly.

Thus, a novel method of pulmonary drug delivery has been shown and described. Various changes and substitutions of equivalents may be made, without departing from the spirit and scope of the inventory. While the invention is described here relative to BDP, it applies to other drugs as well. The invention, therefore, should not be restricted, except by the following claims and their equivalents.

We claim:

1. A method for treating inflammatory lung diseases comprising the steps of:

a) preparing a drug formulation by combining micronized crystalline beclomethasone dipropionate and lactose particles in the size range of 20–100 microns;

b) placing the drug formulation into a dry powder inhaler which provides inhalable drug particles having a mass median diameter of about 0.5–5.8 microns; and c) inhaling the drug particles with an inspiratory flow rate of about 10–60 liters/minute, to produce a deep lung deposition of the inhaled drug particles with a respirable fraction of about 25–45%.

2. The method of claim 1 wherein drug particles are delivered to locations in the lung having reduced mucocilliary clearance or local metabolism, resulting in a kad less than ½ of kad of a metered dose inhaler.

3. The method of claim 1 wherein the level of drug in the lungs one hour after delivery is greater than one-half of the initial level.

4. The method of claim 1 wherein the level of drug in the blood one hour after delivery exceeds 20% of the peak level of drug in the blood.

5. The method of claim 1 wherein the level of drug in the blood 1 hour after delivery exceeds 30% of the peak level of drug in the blood.

6. The method of claim 1 wherein the level of drug in the blood 1 hour after delivery exceeds 10% of the peak level of drug in the blood.

7. The method of claim 1 wherein the level of drug in the blood 2 hours after delivery exceeds 20% of the level of drug in the blood 1 hour after delivery.

8. The method of claim 1 wherein the level of drug in the blood 3 hours after delivery exceeds 10% of the level of drug in the blood 1 hour after delivery.

9. The method of claim 1 wherein the level of drug in the blood 1 hour after delivery exceeds 30% of the level of drug in the blood 30 minutes after delivery.

10. The method of claim 1 wherein the level of drug in the blood falls from a peak value to one-half of the peak value in 30–45 minutes.

11. A method for treating inflammatory lung diseases comprising the steps of:

a) preparing a drug formulation by combining micronized crystalline beclomethasone dipropionate and lactose particles in the size range of 20–100 microns;

b) placing the drug formulation into a dry powder inhaler which provides inhalable drug particles having a mass median diameter of about 0.5–5.8 microns; and c) inhaling the drug particles with an inspiratory flow rate of about 10–60 liters/minute, to produce a deep lung deposition of the inhaled drug particles and with the drug particles delivered to locations in the lung having reduced mucocilliary clearance or local metabolism, resulting in a kad less than ½ of kad of a metered dose inhaler.

12. A method for treating inflammatory lung diseases comprising the steps of:

a) preparing a drug formulation by combining micronized crystalline beclomethasone dipropionate and lactose particles in the size range of 20–100 microns;

b) placing the drug formulation into a dry powder inhaler which provides inhalable drug particles having a mass median diameter of about 0.5–5.8 microns; and c) inhaling the drug particles with an inspiratory flow rate of about 10–60 liters/minute, to produce a deep lung deposition of the inhaled drug particles and wherein the level of drug in the lungs one hour after delivery is greater than one-half of the initial level.

13. The method of claim 12 wherein the level of drug in the blood one hour after delivery exceeds 10% of the peak level of drug in the blood.

14. The method of claim 12 wherein the level of drug in the blood 1 hour after delivery exceeds 30% of the peak level of drug in the blood.

15. The method of claim 12 wherein the level of drug in the blood 2 hours after delivery exceeds 20% of the level of drug in the blood 1 hour after delivery.

16. The method of claim 12 wherein the level of drug in the blood 3 hours after delivery exceeds 10% of the level of drug in the blood 1 hour after delivery.

17. The method of claim 12 wherein the level of drug in the blood 1 hour after delivery exceeds 30% of the level of drug in the blood 30 minutes after delivery.

18. The method of claim 12 wherein the level of drug in the blood falls from a peak value to one-half of the peak value in 30–45 minutes.

* * * * *